(12) United States Patent
Girotra et al.

(10) Patent No.: US 10,478,344 B2
(45) Date of Patent: Nov. 19, 2019

(54) ADHESIVE EARPLUGS USEFUL FOR SEALING THE EAR CANAL

(71) Applicant: Tusker Medical, Inc., Menlo Park, CA (US)

(72) Inventors: Rohit Girotra, San Francisco, CA (US); Bernard H. Andreas, Los Altos, CA (US); Alfredo Cantu, Pleasanton, CA (US); Nikhil Bhat, Fremont, CA (US); Mansour Saleki, San Jose, CA (US); Shrirang V. Ranade, Foster City, CA (US); Miranda Ray, San Jose, CA (US)

(73) Assignee: Tusker Medical, Inc., Menlo Park, CA (US)

( * ) Notice: Subject to any disclaimer, the term of this patent is extended or adjusted under 35 U.S.C. 154(b) by 375 days.

(21) Appl. No.: 15/154,496

(22) Filed: May 13, 2016

(65) Prior Publication Data

US 2016/0361204 A1    Dec. 15, 2016

Related U.S. Application Data

(63) Continuation of application No. 13/827,403, filed on Mar. 14, 2013, now Pat. No. 9,364,648.

(51) Int. Cl.
*A61F 11/06* (2006.01)
*A61F 11/08* (2006.01)
(Continued)

(52) U.S. Cl.
CPC .............. *A61F 11/08* (2013.01); *A61F 11/00* (2013.01); *A61F 11/12* (2013.01); *A61M 31/00* (2013.01);
(Continued)

(58) Field of Classification Search
CPC .......... A61F 11/10; A61F 11/08; A61F 11/14; A61F 11/00; A61F 2011/085;
(Continued)

(56) References Cited

U.S. PATENT DOCUMENTS

| 858,673 A | 7/1907 | Roswell |
| 1,920,006 A | 7/1933 | Dozier et al. |

(Continued)

FOREIGN PATENT DOCUMENTS

| CN | 86105171 A | 3/1987 |
| CN | 2087067 U | 10/1991 |

(Continued)

OTHER PUBLICATIONS

U.S. Appl. No. 60/912,902, filed Apr. 19, 207.
(Continued)

*Primary Examiner* — Ophelia A Hawthorne

(57) ABSTRACT

Systems and methods are provided for sealing an ear canal for retaining a solution in the ear canal. Adhesive earplugs are provided through which the solution can be delivered, and which, following delivery, retain the fluid in the ear canal. The systems and methods may also be useful for delivering an anesthetizing solution to the ear canal of a human patient and for maintaining the solution therein for use with an iontophoresis system for anesthetizing the tympanic membrane.

20 Claims, 14 Drawing Sheets

Related U.S. Application Data

(60) Provisional application No. 61/653,080, filed on May 30, 2012.

(51) Int. Cl.
  *A61M 31/00* (2006.01)
  *A61N 1/30* (2006.01)
  *A61F 11/12* (2006.01)
  *A61F 11/00* (2006.01)

(52) U.S. Cl.
  CPC ........ *A61N 1/306* (2013.01); *A61F 2011/085* (2013.01); *A61M 2202/048* (2013.01)

(58) Field of Classification Search
  CPC ........ A61F 11/12; A61F 11/06; A61F 11/002; A61F 2002/183; A61F 2/18; A61F 6/18; A61N 1/306; A61M 31/00; A61M 2210/0662; A61M 2210/0668; A61M 31/002; A61M 3/0254; A61M 3/0279; H04R 25/652; H04R 25/654; H04R 1/1016; Y10T 29/49826; Y10T 156/1062; Y10T 137/87845; Y10T 29/49; Y10T 29/49572; Y10T 29/49995; Y10T 428/249953
  See application file for complete search history.

(56) References Cited

U.S. PATENT DOCUMENTS

| | | |
|---|---|---|
| 2,458,884 A | 1/1949 | Volkmann |
| 3,741,197 A | 6/1973 | Sanz et al. |
| 3,888,258 A | 6/1975 | Akiyama |
| 3,897,786 A | 8/1975 | Garnett et al. |
| 3,913,584 A | 10/1975 | Walchle et al. |
| 3,948,271 A | 4/1976 | Akiyama |
| 3,991,755 A | 11/1976 | Vernon et al. |
| 4,149,533 A | 4/1979 | Ishikawa et al. |
| 4,206,756 A | 6/1980 | Grossan |
| 4,406,282 A * | 9/1983 | Parker .................. A61F 11/08 128/865 |
| 4,468,218 A | 8/1984 | Armstrong |
| 4,473,073 A | 9/1984 | Darnell |
| 4,552,137 A | 11/1985 | Strauss |
| 4,564,009 A | 1/1986 | Brinkhoff |
| 4,601,294 A | 7/1986 | Danby et al. |
| 4,712,537 A | 12/1987 | Pender |
| 4,964,850 A | 10/1990 | Bouton et al. |
| 4,968,296 A | 11/1990 | Ritch et al. |
| 4,971,076 A | 11/1990 | Densert et al. |
| 5,026,378 A | 6/1991 | Goldsmith, III |
| 5,044,373 A | 9/1991 | Northeved et al. |
| 5,047,007 A | 9/1991 | McNichols et al. |
| 5,053,040 A | 10/1991 | Goldsmith, III |
| 5,107,861 A | 4/1992 | Narboni |
| 5,135,478 A | 8/1992 | Sibalis |
| 5,160,316 A | 11/1992 | Henley |
| 5,254,081 A | 10/1993 | Maurer et al. |
| 5,254,120 A | 10/1993 | Cinberg et al. |
| 5,261,903 A | 11/1993 | Dhaliwal et al. |
| D352,780 S | 11/1994 | Glaeser et al. |
| 5,421,818 A | 6/1995 | Arenberg |
| 5,466,239 A | 11/1995 | Cinberg et al. |
| 5,496,379 A | 3/1996 | Reisinger |
| D378,611 S | 3/1997 | Croley |
| 5,610,988 A | 3/1997 | Miyahara |
| 5,643,989 A | 7/1997 | Del Rio et al. |
| 5,674,196 A | 10/1997 | Donaldson et al. |
| D387,863 S | 12/1997 | Herman et al. |
| 5,707,383 A | 1/1998 | Bays et al. |
| 5,792,100 A | 8/1998 | Shantha |
| 5,804,957 A | 9/1998 | Coin |
| 5,810,848 A | 9/1998 | Hayhurst |
| 5,827,295 A | 10/1998 | Del Rio et al. |
| 5,893,828 A | 4/1999 | Uram |
| 5,979,072 A | 11/1999 | Collins, II |
| D413,923 S | 12/1999 | Phipps et al. |
| D420,741 S | 2/2000 | Croley |
| 6,045,528 A | 4/2000 | Arenberg et al. |
| D424,197 S | 5/2000 | Sydlowski et al. |
| 6,059,803 A | 5/2000 | Spilman |
| D426,135 S | 6/2000 | Lee |
| 6,137,889 A | 10/2000 | Shennib et al. |
| 6,148,821 A | 11/2000 | Falco et al. |
| 6,183,469 B1 | 2/2001 | Thapliyal et al. |
| 6,200,280 B1 | 3/2001 | Brenneman et al. |
| 6,206,888 B1 | 3/2001 | Bicek et al. |
| 6,245,077 B1 | 6/2001 | East et al. |
| 6,251,121 B1 | 6/2001 | Saadat |
| 6,295,469 B1 | 9/2001 | Linkwitz et al. |
| D450,843 S | 11/2001 | McGuckin, Jr. et al. |
| 6,347,246 B1 | 2/2002 | Perrault et al. |
| 6,358,231 B1 | 3/2002 | Schindler et al. |
| 6,440,102 B1 | 8/2002 | Arenberg et al. |
| 6,475,138 B1 | 11/2002 | Schechter et al. |
| 6,512,950 B2 | 1/2003 | Li et al. |
| 6,514,261 B1 | 2/2003 | Randall et al. |
| 6,520,939 B2 | 2/2003 | Lafontaine |
| 6,522,827 B1 | 2/2003 | Loeb et al. |
| 6,553,953 B1 | 4/2003 | Chang |
| 6,640,121 B1 | 10/2003 | Telischi et al. |
| 6,645,173 B1 | 11/2003 | Liebowitz |
| 6,648,873 B2 | 11/2003 | Arenberg et al. |
| 6,663,575 B2 | 12/2003 | Leysieffer |
| 6,682,558 B2 | 1/2004 | Tu et al. |
| 6,770,080 B2 | 8/2004 | Kaplan et al. |
| 6,916,159 B2 | 7/2005 | Rush et al. |
| 7,123,957 B2 | 10/2006 | Avrahami |
| 7,127,785 B2 | 10/2006 | Henley et al. |
| 7,137,975 B2 | 11/2006 | Miller et al. |
| D535,077 S | 1/2007 | James et al. |
| 7,160,274 B2 | 1/2007 | Ciok et al. |
| 7,344,507 B2 | 3/2008 | Briggs et al. |
| 7,351,246 B2 | 4/2008 | Epley |
| 7,381,210 B2 | 6/2008 | Zarbatany et al. |
| D595,410 S | 6/2009 | Luzon |
| 7,563,939 B2 | 7/2009 | Freeman et al. |
| D598,543 S | 8/2009 | Vogel et al. |
| 7,654,997 B2 | 2/2010 | Makower et al. |
| 7,677,734 B2 | 3/2010 | Wallace |
| 7,704,259 B2 | 4/2010 | Kaplan et al. |
| 7,749,254 B2 | 7/2010 | Sobelman et al. |
| D622,842 S | 8/2010 | Benoist |
| 8,052,693 B2 | 11/2011 | Shahoian |
| 8,192,420 B2 | 6/2012 | Morriss et al. |
| 8,249,700 B2 | 8/2012 | Clifford et al. |
| 8,409,175 B2 | 4/2013 | Lee et al. |
| 8,425,488 B2 | 4/2013 | Clifford et al. |
| 8,452,392 B2 | 5/2013 | Morriss et al. |
| 8,498,425 B2 | 7/2013 | Graylin |
| 8,518,098 B2 | 8/2013 | Roeder et al. |
| 8,702,792 B2 | 4/2014 | Shahoian |
| 8,840,602 B2 | 9/2014 | Morriss et al. |
| 8,849,394 B2 | 9/2014 | Clifford et al. |
| 9,011,363 B2 | 4/2015 | Clopp et al. |
| 9,023,059 B2 | 5/2015 | Loushin et al. |
| 9,216,112 B2 | 12/2015 | Clifford et al. |
| 9,364,648 B2 * | 6/2016 | Girotra .................. A61F 11/12 |
| 9,387,124 B2 | 7/2016 | Clifford |
| 9,392,229 B2 | 7/2016 | Morriss et al. |
| 9,707,131 B2 | 7/2017 | Shahoian |
| 9,713,710 B2 | 7/2017 | Morriss et al. |
| 9,833,601 B2 | 12/2017 | Clifford |
| 9,950,157 B2 | 4/2018 | Morriss et al. |
| 10,016,304 B2 | 7/2018 | Ray et al. |
| 10,130,808 B2 | 11/2018 | Kermani et al. |
| 10,195,369 B2 | 2/2019 | Andreas et al. |
| 10,258,776 B2 | 4/2019 | Clifford et al. |
| 2002/0026125 A1 | 2/2002 | Leysieffer |
| 2002/0069883 A1 | 6/2002 | Hirchenbain |
| 2002/0111585 A1 | 8/2002 | Lafontaine |
| 2002/0138091 A1 | 9/2002 | Pflueger |
| 2002/0161379 A1 | 10/2002 | Kaplan et al. |

(56) References Cited

U.S. PATENT DOCUMENTS

| | | |
|---|---|---|
| 2002/0169456 A1 | 11/2002 | Tu et al. |
| 2003/0018291 A1 | 1/2003 | Hill et al. |
| 2003/0060799 A1 | 3/2003 | Arenberg et al. |
| 2003/0093057 A1 | 5/2003 | Zhang et al. |
| 2003/0120292 A1 | 6/2003 | Park et al. |
| 2003/0199791 A1 | 10/2003 | Boecker et al. |
| 2004/0054339 A1 | 3/2004 | Ciok et al. |
| 2005/0094835 A1 | 5/2005 | Doty |
| 2005/0154357 A1 | 7/2005 | Pinel |
| 2005/0182385 A1 | 8/2005 | Epley |
| 2005/0203552 A1 | 9/2005 | Laufer et al. |
| 2005/0235422 A1 | 10/2005 | Wallace |
| 2005/0240147 A1 | 10/2005 | Makower et al. |
| 2006/0142700 A1 | 6/2006 | Sobelman et al. |
| 2006/0155304 A1 | 7/2006 | Kaplan et al. |
| 2006/0177080 A1 | 8/2006 | Smith |
| 2007/0003096 A1 | 1/2007 | Nam |
| 2007/0078372 A1 | 4/2007 | Reddy et al. |
| 2007/0183613 A1 | 8/2007 | Juneau et al. |
| 2007/0233222 A1 | 10/2007 | Roeder et al. |
| 2008/0011308 A1* | 1/2008 | Fleming ............ A61F 11/08 128/864 |
| 2008/0051804 A1 | 2/2008 | Cottler et al. |
| 2008/0058756 A1 | 3/2008 | Smith |
| 2008/0065002 A1 | 3/2008 | Lobl et al. |
| 2008/0107287 A1 | 5/2008 | Beard |
| 2008/0212416 A1 | 9/2008 | Polonio et al. |
| 2008/0262468 A1* | 10/2008 | Clifford ............ A61F 11/002 604/501 |
| 2008/0262508 A1 | 10/2008 | Clifford et al. |
| 2008/0262510 A1 | 10/2008 | Clifford |
| 2009/0163848 A1 | 6/2009 | Morriss et al. |
| 2009/0209972 A1 | 8/2009 | Loushin et al. |
| 2009/0262510 A1 | 10/2009 | Pekkarinen et al. |
| 2009/0270807 A1 | 10/2009 | Mas et al. |
| 2009/0299344 A1 | 12/2009 | Lee et al. |
| 2010/0030131 A1 | 2/2010 | Morriss et al. |
| 2010/0041447 A1 | 2/2010 | Graylin |
| 2010/0061581 A1 | 3/2010 | Soetejo et al. |
| 2010/0198135 A1* | 8/2010 | Morriss ............ A61F 11/00 604/21 |
| 2010/0300460 A1 | 12/2010 | Falco et al. |
| 2011/0001564 A1 | 1/2011 | Hori |
| 2011/0015645 A1 | 1/2011 | Liu et al. |
| 2011/0048414 A1 | 3/2011 | Hoekman et al. |
| 2011/0268303 A1* | 11/2011 | Ahsani ............ H04R 11/02 381/326 |
| 2011/0288559 A1 | 11/2011 | Shahoian |
| 2012/0109070 A1* | 5/2012 | Elsamahy ......... A61M 25/02 604/179 |
| 2012/0310145 A1 | 12/2012 | Clifford et al. |
| 2013/0090544 A1 | 4/2013 | Clifford et al. |
| 2013/0190678 A1 | 7/2013 | Andreas et al. |
| 2013/0197426 A1 | 8/2013 | Morriss et al. |
| 2013/0223702 A1 | 8/2013 | Holsing et al. |
| 2014/0102461 A1 | 4/2014 | Girotra et al. |
| 2014/0194891 A1 | 7/2014 | Shahoian |
| 2014/0276352 A1 | 9/2014 | Kermani et al. |
| 2014/0276906 A1 | 9/2014 | Andreas et al. |
| 2015/0068539 A1 | 3/2015 | Morriss et al. |
| 2016/0375204 A1 | 12/2016 | Andreas et al. |
| 2017/0014272 A1 | 1/2017 | Ray et al. |
| 2017/0028193 A1 | 2/2017 | Morriss et al. |
| 2018/0085563 A1 | 3/2018 | Clifford et al. |
| 2018/0256894 A1 | 9/2018 | Morriss et al. |
| 2018/0304059 A1 | 10/2018 | Clifford et al. |
| 2018/0325737 A1 | 11/2018 | Ray et al. |
| 2019/0083780 A1 | 3/2019 | Kermani et al. |

FOREIGN PATENT DOCUMENTS

| | | |
|---|---|---|
| CN | 2409940 Y | 12/2000 |
| DE | 19618585 | 11/1997 |
| EP | 0214527 A1 | 3/1987 |
| FR | 2526656 | 11/1983 |
| JP | S59-129815 | 8/1984 |
| JP | H 07-116190 A | 5/1995 |
| JP | 2010-524584 | 7/2010 |
| WO | WO 92/10223 | 6/1992 |
| WO | WO 2002/043795 | 6/2002 |
| WO | WO 2006/119512 | 11/2006 |
| WO | WO 2008/030485 | 3/2008 |
| WO | WO 2008/036368 | 3/2008 |
| WO | WO 2008/131195 | 10/2008 |
| WO | WO 2009/010788 | 1/2009 |
| WO | WO 2009/105619 | 8/2009 |
| WO | WO 2010/014894 | 2/2010 |
| WO | WO 2011/081772 | 7/2011 |
| WO | WO 2013/016098 | 1/2013 |
| WO | WO 2013/181009 | 12/2013 |
| WO | WO 2014/158543 | 10/2014 |
| WO | WO 2017/011777 | 1/2017 |

OTHER PUBLICATIONS

Patent Examination Report No. 1 for Australian Patent Application No. 2008242735, dated Aug. 8, 2012, 3 pages.
Patent Examination Report No. 1 for Australian Patent Application No. 2013209354, dated Oct. 13, 2014, 5 pages.
First Office Action for Chinese Patent Application No. 200880020861.9, dated Jul. 12, 2011, 10 pages.
Second Office Action for Chinese Patent Application No. 200880020861.9, dated Dec. 31, 2011, 3 pages.
Search Report for Chinese Patent Application No. 201310047126.X, dated Mar. 6, 2015, 2 pages.
Second Office Action for Chinese Patent Application No. 201310047126.X, dated Mar. 16, 2015, 10 pages.
Office Action for European Application No. 08746237.0, dated Mar. 24, 2016, 3 pages.
Office Action for European Application No. 08746237.0, dated Aug. 4, 2015, 7 pages.
Supplementary Partial Search Report for European Application No. 08746237.0, dated Jun. 30, 2014, 9 pages.
Notification of Reasons for Refusal for Japanese Patent Application No. 2010-504267, dated Nov. 20, 2012, 4 pages.
Notification of Reasons for Refusal for Japanese Patent Application No. 2010-504267, dated Nov. 12, 2013, 4 pages.
International Search Report for International Application No. PCT/US2008/060779, dated Sep. 3, 2008.
Written Opinion for International Application No. PCT/US2008/060779, dated Sep. 3, 2008.
Office Action for U.S. Appl. No. 11/749,733, dated Jun. 10, 2009, 13 pages.
Office Action for U.S. Appl. No. 11/749,733, dated Dec. 2, 2008, 9 pages.
U.S. Appl. No. 61/085,360, filed Jul. 31, 2008.
Patent Examination Report No. 1 for Australian Application No. 2009276384, dated Apr. 14, 2014, 3 pages.
Office Action for Canadian Application No. 2,732,595, dated Dec. 8, 2015, 4 pages.
Office Action for Russian Application No. 2011-07228, dated May 24, 2013.
International Search Report for International Application No. PCT/US2009/052395, dated Nov. 6, 2009.
Written Opinion for International Application No. PCT/US2009/052395, dated Nov. 6, 2009.
Patent Examination Report No. 1 for Australian Application No. 2010337214, dated Feb. 27, 2015, 3 pages.
Office Action for Chinese Application No. 201080065012.2, dated Mar. 31, 2016, 20 pages.
International Search Report for International Application No. PCT/US2010/058718, dated Feb. 17, 2011.
Written Opinion for International Application No. PCT/US2010/058718, dated Feb. 17, 2011.
International Search Report for International Application No. PCT/US2010/042128, dated Aug. 27, 2010.
Office Action for Australian Application No. 2012287268, dated Feb. 11, 2016.

(56) References Cited

OTHER PUBLICATIONS

Office Action for European Application No. 12743007.2, dated Jul. 21, 2016, 5 pages.
Notification of Reasons for Refusal for Japanese Application No. 2014-522882, dated May 31, 2016, English Translation.
International Search Report for International Application No. PCT/US2012/047179, dated Mar. 11, 2013.
Written Opinion for International Application No. PCT/US2012/047179, dated Mar. 11, 2013.
Office Action for U.S. Appl. No. 13/827,403, dated Dec. 4, 2014, 19 pages.
Office Action for U.S. Appl. No. 13/827,403, dated Jul. 8, 2015, 23 pages.
Written Opinion for International Application No. PCT/US2013/041816, dated Sep. 16, 2013, 7 pages.
International Search Report and Written Opinion for International Application No. PCT/US2014/018017, dated May 22, 2014, 12 pages.
International Search Report for International Application No. PCT/US2009/069388, dated Jun. 30, 2010.
Comeau, M. et al., "Local Anesthesia of the Ear by Iontophoresis," vol. 98, Arch. Otolaryngol., pp. 114-120 (Aug. 1973).
Comeau, M. et al., "Anesthesia of the Human Tympanic Membrane by Iontophoresis of a Local Anesthetic," The Larynogoscope, vol. 88, pp. 277-285 (1978).
Echols, D. F. et al., "Anesthesia of the Ear by Iontophoresis of Lidocaine," Arch. Otolaryngol., vol. 101, pp. 418-421 (Jul. 1975).
Epley, J. M., "Modified Technique of Iontophoretic Anesthesia for Myringotomy in Children," Arch. Otolaryngol., vol. 103, pp. 358-360 (Jun. 1977).
Hasegawa, M. et al., "Iontophorectic anaesthesia of the tympanic membrane," Clinical Otolaryngoloy, vol. 3, pp. 63-66 (1978).
Ramsden, R. T. et al., "Anaesthesia of the tympanic membrane using iontophoresis," The Journal of Laryngology and Otology, 56(9):779-785 (Sep. 1977).
"Definition of Plenum," Compact Oxford English Dictionary [online], Retrieved from the Internet: <http://oxforddictionaries.com/definition/english/plenum>, Retrieved on Aug. 6, 2012, 2 pages.
"Definition of Plenum," Merriam-Webster's Online Dictionary, 11th Edition [online], Retrieved from the Internet: <http://www.merriam-webster.com/dictionary/plenum>, Retrieved on Aug. 14, 2012, 1 page.
Medtronic XOMED, "Activent® Antimicrobial Ventilation Tubes," Rev. 1.1, pp. 1-4, 2002, Jacksonville, FL.
Micromedics Innovative Surgical Products, "Micromedics Tympanostomy Tubes," [online], Retrieved on Jul. 15, 2010, Retrieved from the Internet <URL: http://www.micromedics-usa.com/products/otology/micromedicstubes.htm>, 7 pages.
International Search Report dated Sep. 16, 2013 corresponding to International Application PCT/US2013/041816, filed May 20, 2013.
Chinese Office Action issued by the Chinese Patent Office for Application No. 201380027926.3, dated May 3, 2016.
Office Action for Australian Application No. 2013267734, dated Nov. 8, 2016, 4 pages.
Office Action for Chinese Application No. 201380027926.3, dated Jan. 16, 2017, 16 pages.

* cited by examiner

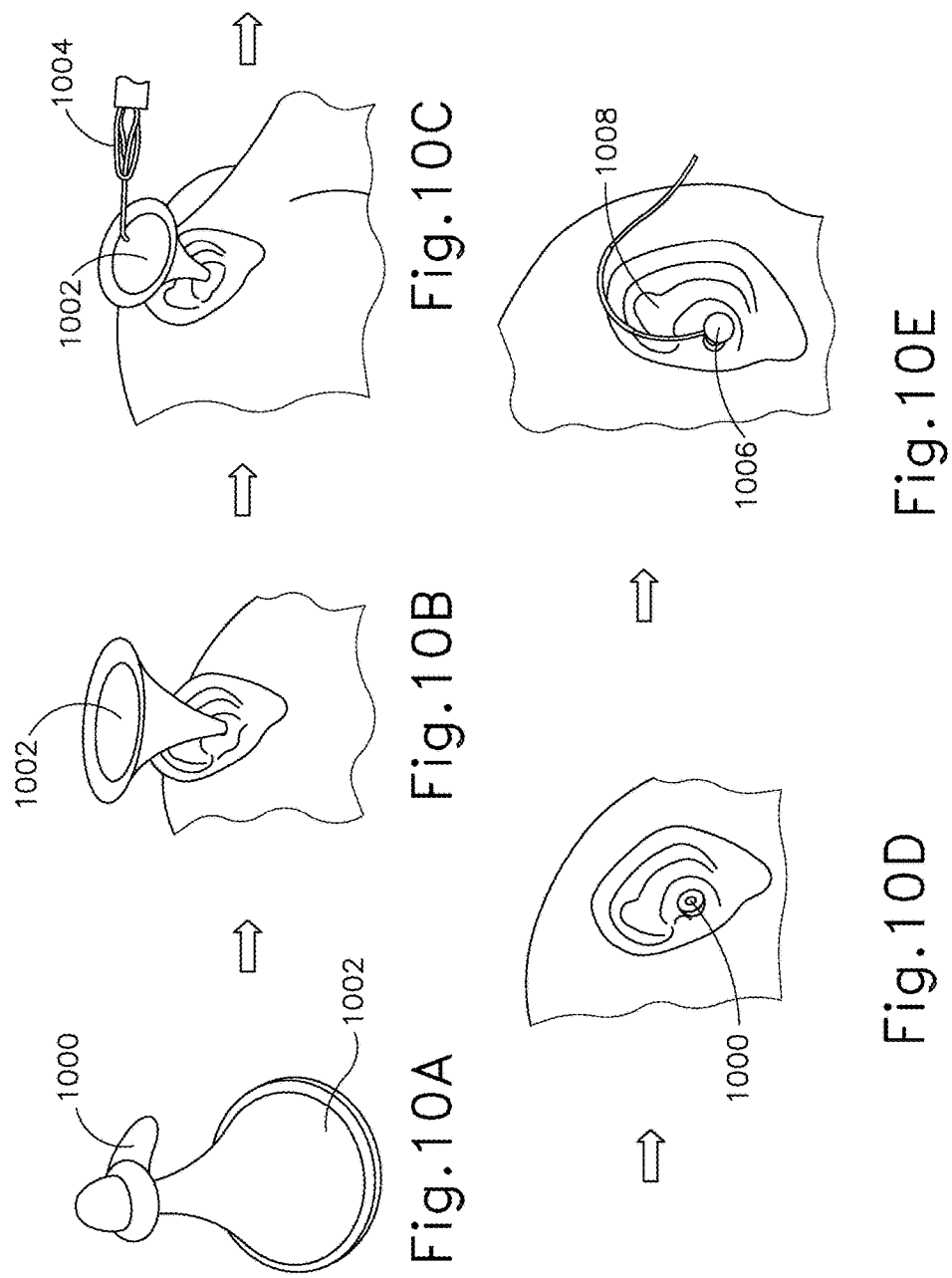

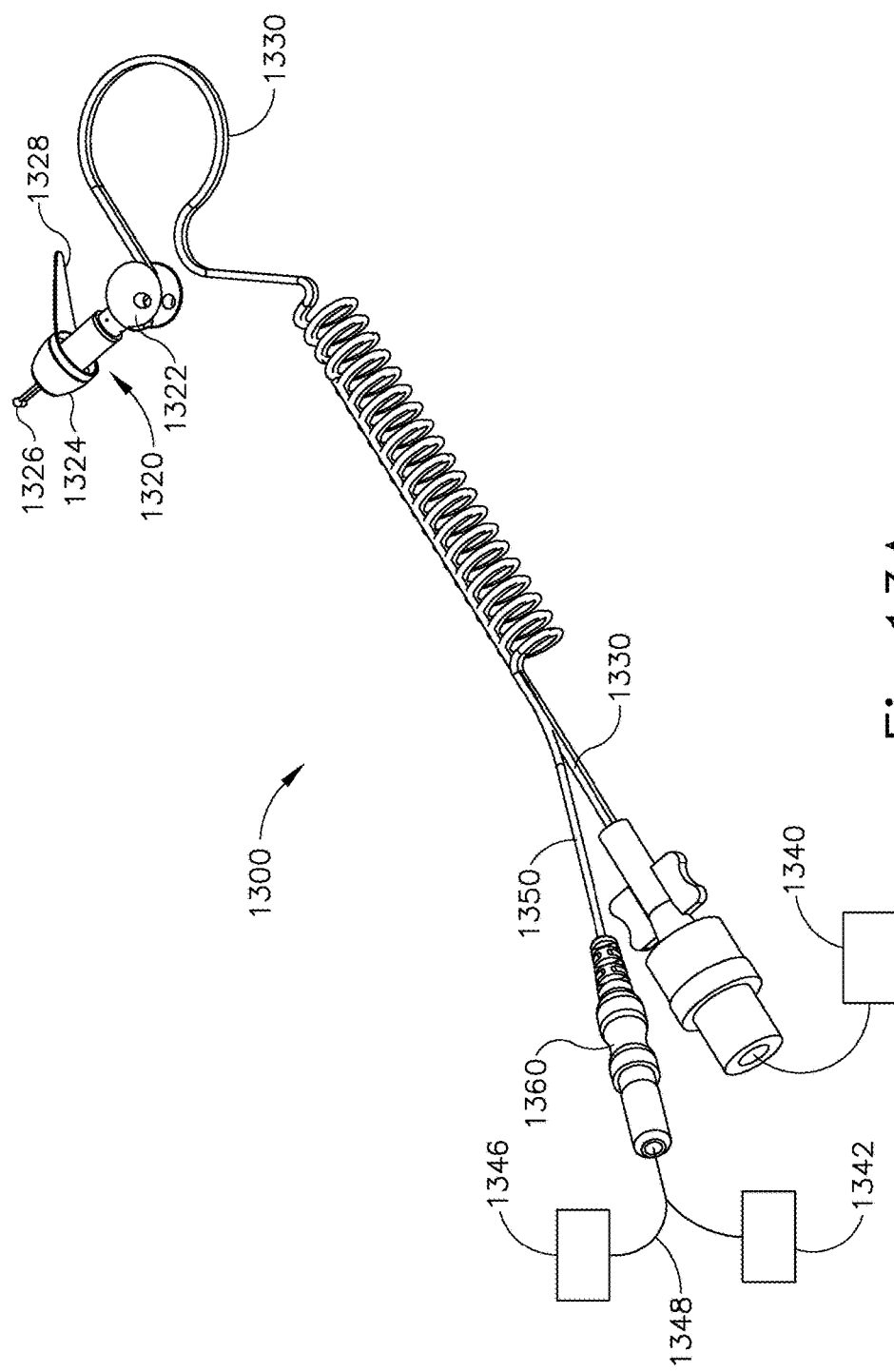

ADHESIVE EARPLUGS USEFUL FOR SEALING THE EAR CANAL

CROSS-REFERENCE TO RELATED APPLICATIONS

This application is a continuation of and claims priority to U.S. patent application Ser. No. 13/827,403, filed Mar. 14, 2013, entitled "Adhesive Earplugs Useful for Sealing the Ear Canal," which claims priority to and the benefit of U.S. Provisional Patent Application No. 61/653,080, filed May 30, 2012, entitled "Adhesive Earplugs Useful for Sealing the Ear Canal," the contents of each of which are incorporated herein by reference in their entirety.

TECHNICAL FIELD

The present invention is generally related to medical devices and apparatus and in particular, for devices and methods for filling and retaining a solution in the ear canal of a human patient.

BACKGROUND

The present invention provides systems and methods useful for delivering fluids to the ear canal of a patient. The systems and methods may be useful for anesthetizing the tympanic membrane and/or the ear canal of a patient in preparation for a surgical procedure, including the placement of a tympanostomy tube (or pressure equalization tube) across a tympanic membrane of an ear. Additionally, the invention provides systems and methods for delivering and/retaining fluid in the ear canal of a human patient for treatment of the ear canal or tympanic membrane.

Otitis media is among the most common diagnoses made by pediatricians. A majority of children may have at least one episode of otitis media ("ear infection") prior to their third birthday. Otitis media is often caused by an inability of the Eustachian tube to drain fluid from the middle ear. Otitis media is often treated with antibiotics.

A significant number of children exhibit recurrent episodes of otitis media and/or otitis media with effusion. Treatment of these more severe cases often involves the placement of a tympanostomy tube across the tympanic membrane to provide adequate drainage and/or ventilation of the middle ear and reduce the likelihood of future infections. Tympanostomy tubes provide fluid communication between the middle and outer ear (e.g., pressure equalization) and typically fall out spontaneously within about a year of placement. Tympanostomy tube placement is among the most frequent surgical procedures performed in the pediatric population. It has been estimated that more than a million tympanostomy tubes may be placed each year, with typical patients being between about 18 months and 7 years of age at the time of the procedure.

Tympanostomy tube placement is typically performed in an out-patient surgery setting under general anesthesia. After administering the general anesthesia, the physician typically first examines the external auditory canal and tympanic membrane under microscopic visualization through a hand-held conical shaped speculum. The physician then makes an incision in the tympanic membrane (a "myringotomy"), typically using a standard, small profile scalpel which the physician advances through the conical speculum. The physician may then pass a suction device through the myringotomy into the middle ear, to aspirate fluid/effusion from the middle ear. The physician will then place the tympanostomy tube across the tympanic membrane, typically using a basic tool, such as forceps, for holding and advancing the tube into the myringotomy.

Systems and methods have been proposed for deploying tympanostomy tubes without having to use general anesthesia. Such systems are described for example in US Publication No. 2011/001564 (Tympanic Membrane Pressure Equalization Tube Delivery System), US Publication No. 2010/0198135 (Systems and Methods for Anesthetizing Ear Tissue), US Publication No. 2009/0163848 (Iontophoresis Methods) and US Publication No. 2009/0262510 (Disposable Iontophoresis System and Tympanic Membrane Pain Inhibition Method) each of which is incorporated by reference in their entirety. These publications describe integrated methods for delivering tympanostomy tubes and appropriate anesthesia, however, simplified systems that provide for delivery of solution to the tympanic membrane with minimal discomfort to the patient are still desirable.

In light of the above, the present inventions are directed to improved devices, systems, and methods for delivering and retaining fluid in the ear canal of a patient. These improvements facilitate delivery and retention of an anesthetizing solution into the ear canal to prepare the tympanic membrane for tympanostomy tube placement without requiring multiple devices and operator-performed steps. At least some of these advantages may be provided by the embodiments described herein.

SUMMARY

The present invention provides systems and methods for use in delivering a solution to and retaining a solution in the ear canal of a human patient.

In one aspect, the invention is directed to an earplug having a dome shaped portion for insertion into the ear canal. The dome shaped portion has an outside surface and an inside surface. The earplug further has a flap useful for removal of the earplug from the ear canal. A pressure sensitive adhesive on the outside surface of the dome shaped portion contacts the ear canal such that the earplug is retained in the ear canal for a period of time.

In one embodiment, the earplug has a flange that surrounds the dome shaped portion. In another embodiment, the flange is a 360 degree flange that surrounds the dome shaped portion and in yet another embodiment, the flange is a 180 degree to less than 360 degree flange that partially surrounds the dome shaped portion.

In a further embodiment, the earplug flange has notches, and in another embodiment the flange has 1 to 6 notches.

In yet another embodiment, the earplug has a shaft portion for connection to a handle through which the solution is delivered into the ear canal, the shaft portion being contained within the inside surface of the dome shaped portion.

In another embodiment, the pressure sensitive adhesive on the earplug is selected from the group consisting of silicones, acrylics, butyl rubber, ethylene-vinyl acetate, natural rubber, nitriles and styrene block copolymers.

In yet another embodiment, the pressure sensitive adhesive is a silicone pressure sensitive adhesive.

In a further embodiment, the solution is selected from the group consisting of an anesthetizing solution, an antibacterial solution, an antifungal solution, an anti-inflammatory solution and a ceruminolytic solution.

In still another embodiment, the solution is an anesthetizing solution that is selected from the group consisting of lidocaine, the combination of lidocaine and epinephrine, and the combination of lidocaine, epinephrine and sodium bicarbonate.

In another aspect, the invention is directed to a system for delivering a solution to the ear canal of a human patient and for retaining the solution therein. The system includes an earplug for use in retaining a solution in the ear canal of a human patient, the earplug having a dome shaped portion for insertion into the ear canal. The dome shaped portion has an outside surface and an inside surface, a flap useful for removal of the earplug from the ear canal, a shaft, and a pressure sensitive adhesive on the outside surface of the dome. The system further includes a handle for inserting the earplug into the ear canal of the patient, the handle being inserted into the shaft of the earplug and having a fill system wherein the solution is delivered through the handle and the shaft of the earplug into the patient's ear canal.

In one embodiment, the earplug has a flange that surrounds the dome shaped portion.

In another embodiment, the handle further has vent features. In a further embodiment, the vent features may be vent holes or vent slits or a combination thereof.

In another embodiment, the handle further has a fill tip.

In still another embodiment the handle further comprises electrodes useful for iontophoretic delivery of the solution to the tympanic membrane.

In yet another aspect, the invention is directed to a method for filling and retaining an anesthetizing solution in the ear canal of a human patient. The method includes preparing an anesthetizing solution, preparing the ear canal of a human patient for delivery of the anesthetizing solution, selecting an earplug having adhesive thereon based on the determined appropriate earplug size, assembling an ear kit system using the selected earplug, inserting the earplug into the ear canal of the human patient and adhering the earplug to the ear canal, and powering on a control unit to begin an iontophoresis procedure to deliver the anesthetizing solution to the tympanic membrane.

In one embodiment, the anesthetizing solution is selected from the group consisting of lidocaine, the combination of lidocaine and epinephrine, and the combination of lidocaine, epinephrine and sodium bicarbonate.

In another embodiment, preparing the anesthetizing solution includes warming it to body temperature.

In yet another embodiment, assembling the ear kit system includes removing the earplug with adhesive thereon from a packaging system, exposing the adhesive, and positioning the earplug.

In another aspect, the invention is directed to a method of filling and retaining a solution in the ear canal of a human patient. The method includes preparing a therapeutic solution, preparing the ear canal of a human patient for delivery of the therapeutic solution, selecting an earplug having adhesive thereon based on the determined appropriate earplug size, assembling the earplug on an ear kit system using the selected earplug, inserting the earplug into the ear canal of the human patient and adhering the earplug to the ear canal, wherein the solution is selected from the group consisting of antifungal agents, antibacterial agents, anti-inflammatory agents, antibiotic agents, steroids, astringent, and ceruminolytics.

In another aspect, the invention is an earplug system for use in retaining a solution in the ear canal of a human patient. The earplug system comprises an earplug having an outside surface for contacting the ear canal. The earplug comprises a dome shaped portion for insertion into the ear canal, a flap connected to the dome shaped portion; and a pressure sensitive adhesive adhered to the outside surface of the earplug. The earplug system further comprises a handle for inserting the earplug into the ear canal; and tubing for delivering the solution through the earplug and the handle and into the ear canal. In one embodiment, the earplug system further comprises a pressure applicator for activating the pressure sensitive adhesive and in another embodiment, the earplug system further comprises a liner for protecting the pressure sensitive adhesive during storage and insertion of the earplug into the ear canal.

In one embodiment the earplug system tubing is routed through the handle and exits the handle at an angle of between about 10 and 30 degrees. In another embodiment, the earplug system conforms to different anatomy. In yet a further aspect the solution is an anesthetizing solution.

In another aspect, the invention is a method for retaining a solution in the ear canal of a human patient. The method comprises providing an earplug system comprising an earplug having an outside surface for contacting the ear canal. The earplug comprises a dome shaped portion for insertion into the ear canal; a flap connected to the dome shaped portion; and a pressure sensitive adhesive adhered to the outside surface of the earplug. The earplug system further comprises a handle for inserting the earplug into the ear canal and tubing for delivering the solution through the earplug and the handle and into the ear canal. The method further comprises inserting the earplug system into the ear canal and delivering the solution into the ear canal.

For a further understanding of the nature and advantages of the invention, reference should be made to the following description taken in conjunction with the accompanying figures. However, each of the figures is provided for the purpose of illustration and description only and is not intended to limit the scope of the embodiments of the present invention.

BRIEF DESCRIPTION OF THE DRAWINGS

FIGS. 10A, 10B, 10C, 10D and 10E show perspective views of a further method for filling the ear canal according to the invention.

FIG. 13A shows a perspective view of an earplug assembly according to another embodiment of the invention.

DETAILED DESCRIPTION

The embodiments of the invention are intended to provide systems that are useful for delivering and retaining a solution in a patient's ear.

Figure 1A:
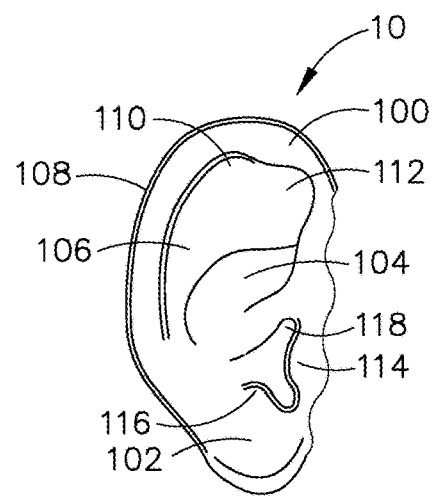
FIG. 1A shows a frontal view of an outer ear.

FIG. 1A shows a view of an outer ear 10. The outer ear 10 includes a major element known as the auricle 100. The outer ear serves as a funnel for directing sounds into the internal portions of the ear. The major physical features of the ear include the lobule, 102, concha 104, antihelix 106, helix 108, scapha 110, triangular fossa 112, tragus 114, antitragus 116 and ear canal 118.

Figure 1B:
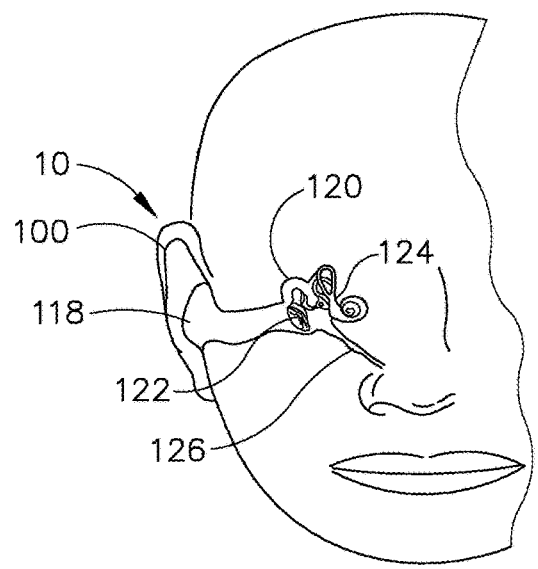
FIG. 1B shows a partial cross-sectional view of an outer, middle and inner ear.

FIG. 1B shows a cross-section of the inner and outer portions of the ear. The outer ear 10 is shown connected to the ear canal 118. The ear canal is shown as a relatively straight passage, but is often a more curved, tortuous passageway. The ear canal is connected to the middle ear 120, which includes the tympanic membrane 122. The middle ear 120 in turn is connected to the internal ear 124 which leads to the auditory tube 126 (also known as the Eustachian tube). The middle ear 120 normally has a pocket of air behind the tympanic membrane 122. When the middle ear 120 is infected, fluid swells inside the tympanic membrane 122. Fluid expansion causes extreme pain to an individual with a middle ear infection, as often occurs in young children.

The anatomy of the ear canal 118 and the tympanic membrane 122 is quite variable across individuals of different ages, and even among those of the same age. The length and diameter of the ear canal 118 may vary, as well as its shape. Further, the size and position of the tympanic membrane 122 is not constant. Accordingly, it would be useful for treatment of middle ear infection, to be able to develop a system for delivering and maintaining fluid in the ear canal for treatment of the ear canal or tympanic membrane that would be comfortable for the patient and would prevent fluid from leaking out of the ear canal. One such use for the system would be for anesthetizing the tympanic membrane prior to delivery of tympanostomy tubes.

Figure 2:
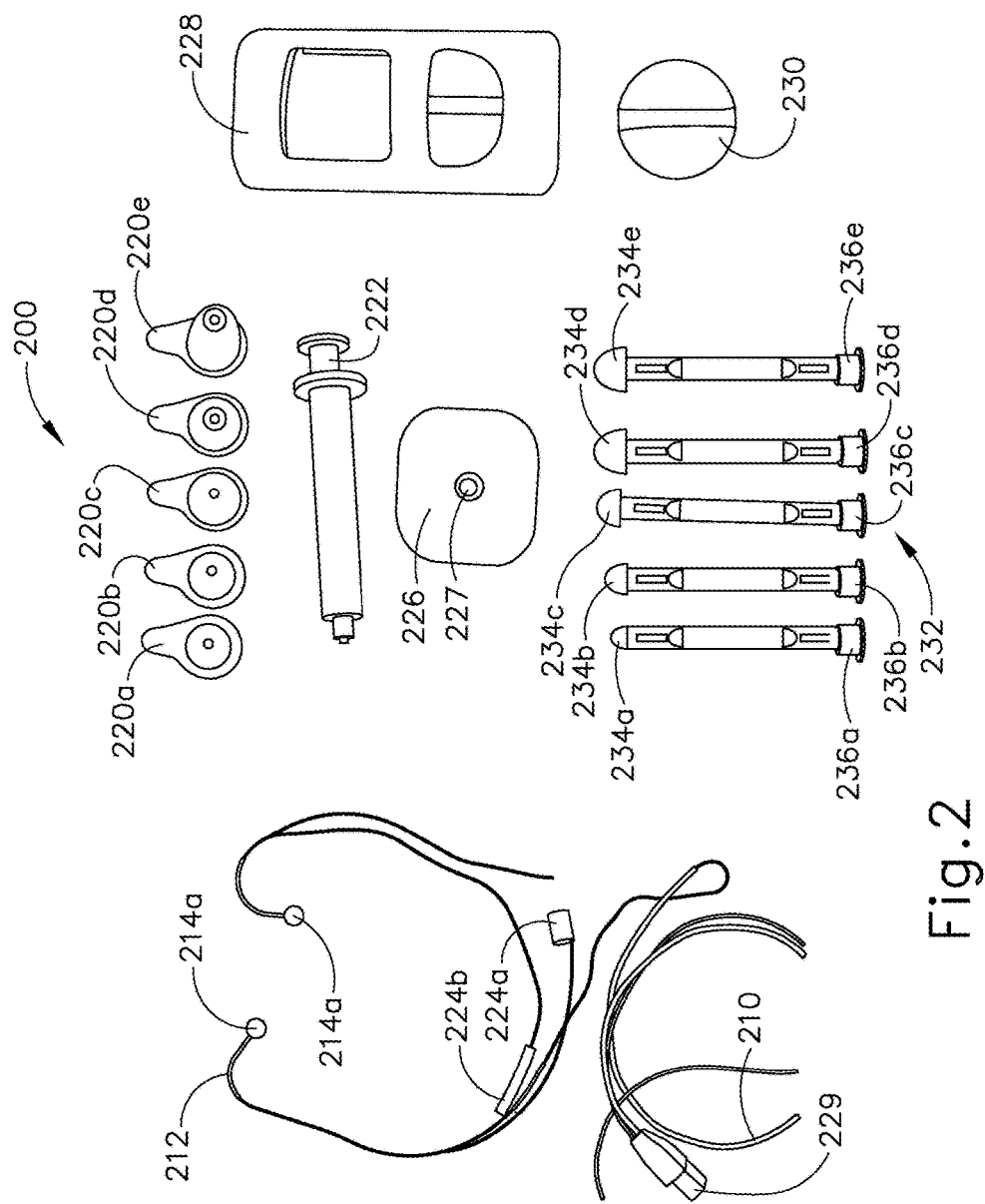
FIG. 2 shows a system for iontophoretic substance delivery.

FIG. 2 shows a system for delivering and maintaining fluid in the ear canal for anesthetizing the tympanic membrane using an iontophoresis delivery system according to one embodiment of the invention. The iontophoresis ear kit system 200 consists of a cable 210, control unit 228, a fill tube and wire system 212 including handles (grips) 214a and 214b, and iontophoresis electrodes (not shown). The system is designed to fill and retain solution in the ear canal and deliver electric charge to the ionized drug solution. Additionally shown in FIG. 2 are a set of earplugs 220a-e, a syringe 222 for attachment to the luer connectors 224a and 224b on the fill tube and wire system 212, and return electrode 226. FIG. 2 further shows an iontophoresis control unit 228, a wire and tube management unit 230, in this case a tie, and a set of earplug sizers 232.

Turning now to a more detailed explanation of the system shown in FIG. 2, the set of ear plug sizers 232 are shown with 5 earplug sizers 234a, 234b, 234c, 234d, and 234e that will aid in determining which size earplug will best fit the patient's anatomy. The earplug sizers 234a-e are provided with lugs 236a-e and ear plugs 220a-e. In the illustrative embodiment, there are 5 different earplug sizes, but in other embodiments there may be 1, 2, 3, 4, 6, 7, 8 or even more than 8 earplug sizes. The lugs 236a-e are constructed, for example, of a rigid plastic material for insertion past the concha 104 (see FIG. 1A) and into the ear canal (118) for initial selection of the size of the earplugs 220a-e. The outer diameters of the lugs are equivalent to the sealing diameters of the earplugs. In an alternative embodiment, the lugs may be constructed of a flexible material such as silicone rubber and have the same shape as the ear plugs.

Figure 3:
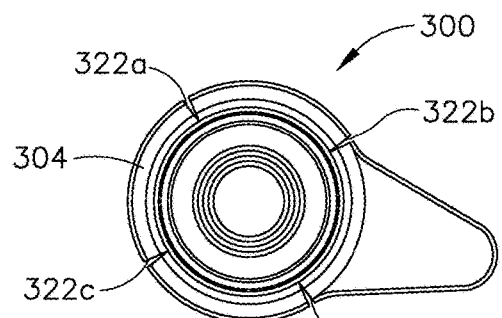
FIG. 3 shows a bottom view of an earplug according to one embodiment of the invention.
Figure 4:
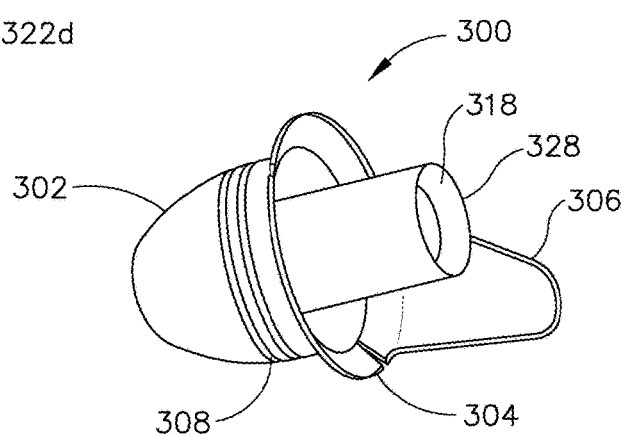
FIG. 4 shows a perspective view of the earplug shown in FIG. 3.

An exemplary earplug 300 is further shown in FIG. 3. The earplug 300 is designed to provide adequate surface area for the placement of sufficient adhesive for sealing of the ear canal, and to provide for a feature that will allow for easy removal of the earplug 300 from the ear canal. Accordingly, the earplug is made of a flexible material that can conform to the contours of the ear canal and may be made of silicone rubber or other similar materials such as polyurethane, styrene butadiene, butyl and fluorosilicone rubbers. As can be further seen in FIGS. 4 and 5, each earplug 300 is constructed of a dome shaped 302 distal portion 312 for insertion into the ear canal 118 and orientation toward the tympanic membrane 122 (see FIG. 1B) and a proximal portion 314. The proximal portion 314 of the dome 302 has a flange 304 that surrounds it. Further, a shaft section 318 disposed within the dome shaped section 302 can be attached at its distal end to the distal end of the dome shaped section 302 and at its proximal end 328 to the earplug sizer 234a-e (See FIG. 2) or to the outside surface of the handle 316 which contains the electrode.

The earplug 300 provides a seal to keep liquid in the ear canal for a period of time of at least about 1 minute, often at least about 5 minutes, often at least about 10 minutes, often at least about 30 minutes and often at least about 60 minutes. In some cases, the liquid is a drug solution useful for anesthetizing the tympanic membrane. The earplugs include an adhering substance for adhering the earplugs to the ear canal. The adhering substance must adhere to the earplug substrate as well as the outer ear canal skin (the concha, see FIG. 1A). The adhering substance must be more adhesive to the earplug 300 than to the concha 104 and must allow for peeling off and repositioning of the earplug 300 within the ear canal and further must adhere to both wet and dry skin. The adhering substance may be a two-sided tape or a pressure sensitive adhesive. In a particular embodiment, the earplugs are coated with a pressure sensitive adhesive (PSA) 320 that secures them in the ear canal. Representative pressure sensitive adhesives include but are not limited to silicones, acrylics, butyl rubber, ethylene-vinyl acetate, natural rubber, nitriles and styrene block copolymers, and in particular may be silicone rubbers manufactured by Dow-Corning under the trade names of MD7-4602 or MD7-4502 or manufactured by NuSil Corporation under the trade name of MED-1356. Multiple color-coded earplug sizes are available to accommodate variation in ear canal size.

Figure 14A:
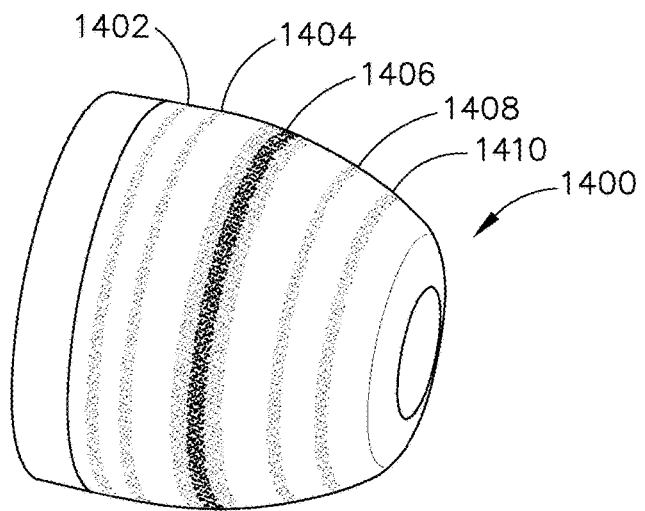
FIGS. 14A and 14B are perspective views of adhesive earplugs according to an embodiment of the invention.
Figure 14B:
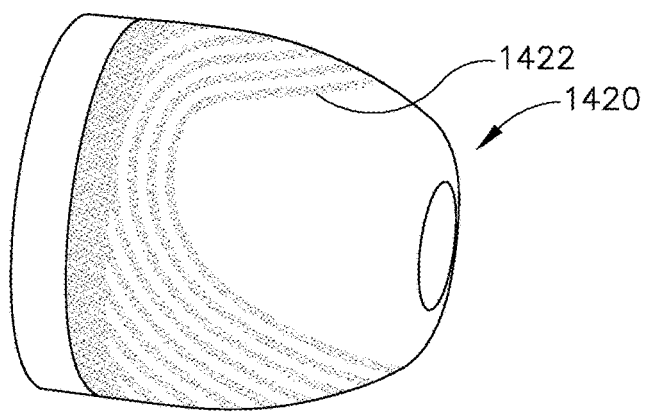

The earplugs 300 are designed to have a dome shape 302 and a flange 304 surrounding the dome 302. The flange may further have a flap 306 which extends beyond the circumference of the rest of the flange. The PSA may be applied in bead form, ring form or brushed on. In the embodiment shown in FIG. 5, three rings 308 of PSA surround the proximal portion 314 of the dome. The PSA 320 may be applied in 1 or more rings (1, 2, 3, 4 or 5) often in 3 rings, or 2 to 4 rings or even 1 to 5 rings. In one aspect, the PSA may be applied to the earplug 1400 in a patterned manner as shown in FIG. 14A with two thin bands 1402 and 1404 on one side of a thicker band 1406 and two thin bands 1408 and 1410 on the other side of the thicker band 1406 and to the earplug 1420 in a contoured manner 1422 as shown in FIG. 14B, such that the earplug 300 can be positioned before the PSA is in contact with the skin. Further, the PSA may be applied in greater quantity in certain areas to match the anatomical structures within the ear. The PSA 320 may also be applied in partial rings or in spots. The PSA 320 can be applied either to the dome section 302 of the earplug 300 or the flange section 304 of the earplug 300 or to both the flange and the dome sections of the earplug. The PSA 320 sticks to the ear canal walls and the outside ear and provides retention for the earplug 300. It prevents the iontophoresis drug solution from coming out of the ear.

Prior to insertion of the earplug 300 into the ear canal, a liner may be used to protect the PSA from adhering. The liner is removed prior to final placement of the earplugs. In an alternative embodiment, the adhesive formulation may be replaced with a formulation that is modified to contain groups or chemical moieties that will change their tack to the skin upon application of an external signal. This signal may be chemical (such as presence of absence of a solvent that causes swelling), thermal (lowering or increase of temperature), electrical, mechanical (change in stress or strain), magnetic or optical. The change in surface adhesive property (amount of adhesive force between adhesive layer and skin) would occur upon application of the external signal, thereby allowing for replacement or repositioning of the earplug 300 in the ear canal.

An example of a system that can change in response to an external signal is the use of a solvent system that is volatile at body temperatures (for easy removal). The presence of solvents (including but not limited to alcohols or ketones, more specifically a mixture of alcohol and de-ionized water or low boiling point alcohols such as ethanol or isopropyl alcohol or a solvent such as acetone) lowers the adhesion by making the polymer molecules highly mobile and leads to lower interaction with the substrate. Removal of the solvent would lower the mobility and lead to a higher degree of interaction between the polymer chains in the adhesive and the substrate, thereby leading to a higher adhesive force.

In an alternative embodiment, the adhesive may be replaced with self-expanding sections on the earplugs themselves. These self-expanding sections may be made from any self-expanding material, including but not limited to polymeric materials, and metallic materials such as nitinol in the form of a ring attached to the earplug.

Figures 11A, 11B, 11C, 11D, 11E:
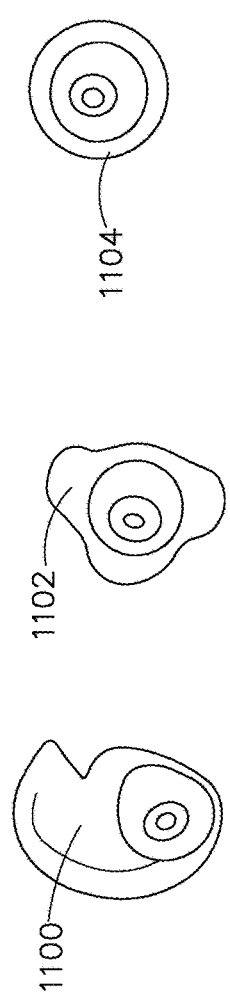
FIGS. 11A, 11B, 11C, 11D and 11E show perspective views of a number of different embodiments of the earplugs according to the invention.

The flange 304 can be designed to be a continuous 360 degree flange that surrounds the earplug dome 302 or it can have notches or cuts at different locations for relieving stress on the earplug 300 or for preventing pleating when the earplug 300 is compressed prior to being inserted in the ear canal or while positioned within it. In addition, as shown in FIGS. 11A, 11B, 11C, 11D and 11E, the flange 304 may have a number of different configurations including but not limited to a concha shape 1100, to follow the contour of the concha (FIG. 11A), a three finger design 1102 (FIG. 11B), an oval two finger design 1106 and a rectangular two finger design 1108 (FIGS. 11D and 11E) and a round flange design 1104 with no flaps or fingers (FIG. 11C). In addition to the two finger designs 1106 and 1108 and three finger design 1102 shown, any number of fingers from 4 to 6 fingers or more are contemplated. Additionally, the earplug may be designed to fit over the tragus 114 alone or to both the concha 104 and the tragus 114 (see FIG. 1A). Where the earplug is designed to fit over the concha 104, the earplug may include trim lines, such that the earplug may be trimmed along predetermined portions to an appropriate earplug for the size and shape of a particular patient's concha.

Figure 5:
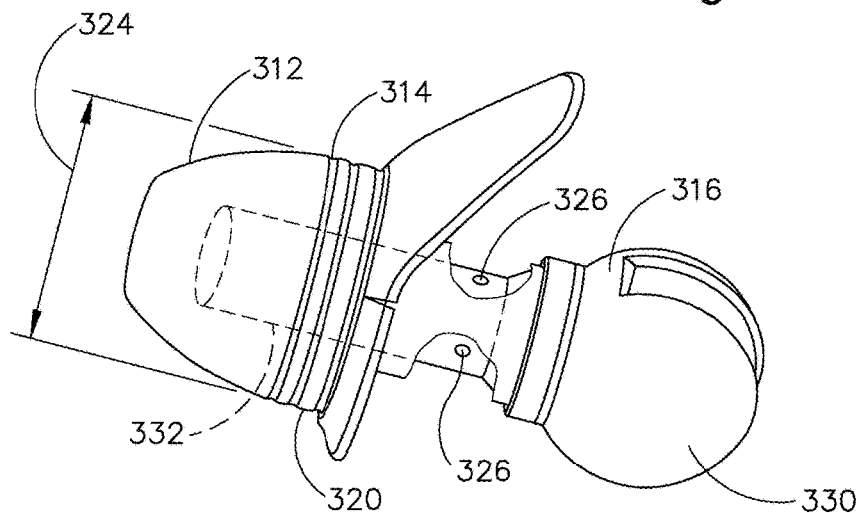
FIG. 5 shows a perspective view the earplug of FIG. 3 further including a handle according to the invention.

FIG. 3 shows the flange 304 with 4 notches 322a, b, c and d, but the flange may have any number of notches such as 1, 2, 3, 5 or 6 notches. It can also be designed to be less than 360 degrees to partially surround the dome shaped portion such as from 180 degrees to less than 360 degrees. The flap 306 is an aid that allows for the ease of removal of the earplug 300 from the ear canal. The flap 306 allows the health care professional to peel the plug from the ear canal. It can be designed to be an integral part of the earplug or a separate component and attached to the earplug 300 rather than molded with the earplug. As shown in FIG. 5 an exemplary dome shaped ear plug 300 has a sealing diameter (SD) 324 that fits against the ear canal for sealing the iontophoresis solution into the ear canal. The flange 304 provides an additional area for presence of PSA 320 and helps in increasing the surface area for PSA 320. The PSA application on the earplug helps in sticking the plug to the ear canal walls. The notches 322a-d on the flange 304 help reduce the pleating in the flange 304 which may occur during insertion and retention in the ear canal due to the oval nature of the ear canal in some people. The flap 306 is designed to be easy to grip, non-intrusive and comfortable. Pulling on the flap 306 leads to peeling of the earplug 300, allowing for comfortable removal of the earplug 300 from the ear canal.

Use of PSA to secure the earplug serves to eliminate the need for further retention elements like a headset. PSA application is a process challenge because of the three dimensional geometry of the earplug. The method of using a dispensing system similar to the one manufactured by EFD Corporation to apply beads of the adhesive as well as the method of brushing the PSA on the earplug enhances the manufacturability of the earplug.

The flange 304 provides an additional area for presence of PSA 320 and helps in increasing the surface area for PSA 320. The PSA application on the earplug helps in sticking the plug to the ear canal walls. The notches 322a-d on the flange 304 help reduce the pleating in the flange 304 which may occur during insertion and retention in the ear canal due to the oval nature of the ear canal in some people. The flap 306 is designed to be easy to grip, non-intrusive and comfortable. Pulling on the flap 306 leads to peeling of the earplug 300, allowing for comfortable removal of the earplug 300 from the ear canal.

Figure 12:
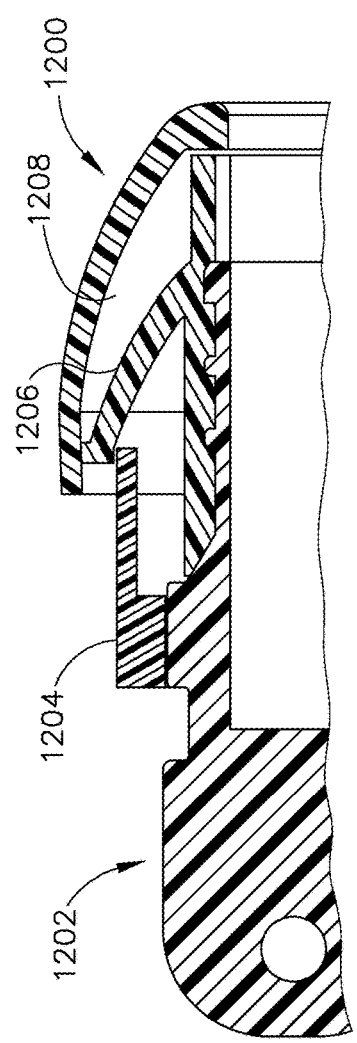
FIG. 12 is an enlarged cut-away view of an earplug including a handle according to a further embodiment of the invention.

In an alternative embodiment, an adjustable ear plug design may be desirable, and that may require the use of pressure sensitive adhesive or may not require such use. The design is shown in FIG. 12 and includes an earplug 1200, an earkit handle 1202, a lever 1204, and a flap 1206. The flap 1206 is shaped like an umbrella and is made of an elastomer with higher durometer than the earplug 1200. In use, the flap 1206 engages the inner surface 1208 of the earplug 1200. The lever 1204 is engaged with the earkit handle 1202 in a threaded fashion. Following insertion into the ear canal, there will be a slight clearance between the earplug 1200 and the ear canal. The lever 1204 is then rotated clockwise to advance the lever 1204 toward the ear drum. As the lever advances forward, it opens the flap 1206. The flap 1206 presses against the inner surface 1208 of the earplug 1200 and stretches the earplug 1200 to fit against the ear canal. Using a buttress thread as the threaded interface between the lever 1204 and the handle 1202 reduces the possibility of backward movement of the earplug 1200, ensuring continued sealing of the ear canal.

Excessive pressure buildup in the ear canal can cause patient discomfort and is not desirable. To prevent excessive pressure buildup the ear kit handle 316 is designed to include vent features 326 (which can include but are not limited to holes or slits or a combination thereof) which provide a pathway for venting the air and fluid during iontophoresis solution delivery. In the embodiment shown in FIG. 5, the vent features comprise holes which can vary in diameter from 0.005 inches to 0.030 inches. Depending on the maximum pressure requirements either one hole or multiple holes (2 are shown but there can be 3, 4 or more) can be positioned along the handle (see FIG. 5). Furthermore, the interference between the earplug shaft 318 and the ear kit handle 316 can be varied depending on the maximum pressure requirements. The vent features 326 are covered by the earplug shaft 318 and the earplug shaft 318 acts like a valve to allow for venting when the physician is filling the ear canal and prevents leakage when the therapy is on-going.

The handle 316 is designed to allow for ergonomic gripping of the device for ease of insertion of the earplug 300 into the ear canal. The grip 330 is designed as a rounded elbow, however it could be flat and rectangular as well, so long as it is easy to grip and small enough not to interfere with the operation of the fill tube and wire system 212. The handle 316 distal end 332 also includes mating features for interfacing with the earplug 300 and a cavity for positioning and seating the electrode. The fill tube and wire system 212 is designed to include one or more spray holes and extends from the handle about 0.4 inches. It is shaped to route behind the ear (see FIG. 6) and has luer connectors 224a and 224b for easy connection and removal of the syringe 222. The electrode (not shown) is a coiled silver wire that resides inside of the handle 316 and provides adequate surface area for the iontophoresis reaction.

Figure 6:
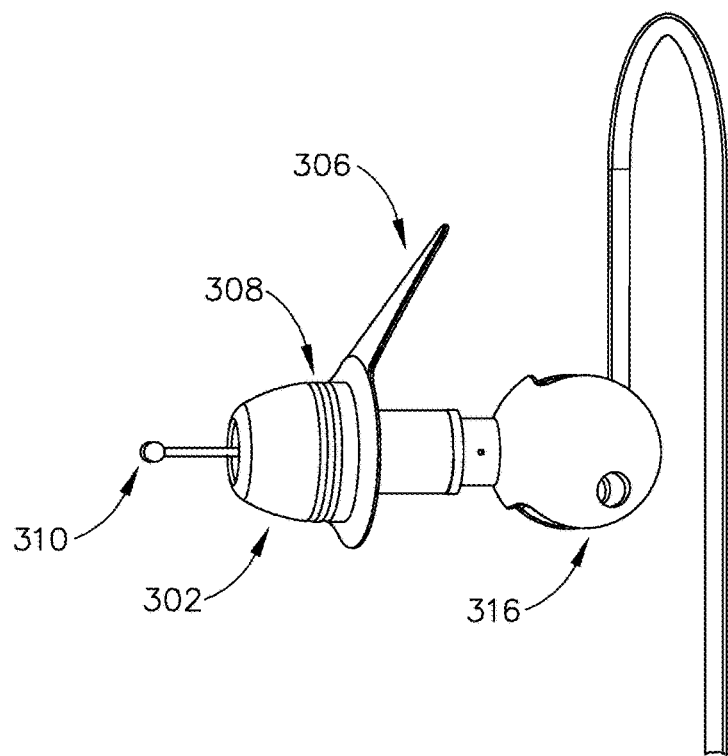
FIG. 6 shows a perspective view of the earplug and handle of FIG. 5 further including the accompanying wire and tubing for iontophoretic substance delivery.

FIG. 6 shows the earplug 300 seated on the handle 316 with the fill tip 310 extending through the shaft section 318 of the earplug 300 and beyond the distal portion 312 of the dome 302. The three spray holes distributed 120 degrees apart on the fill tip 310 provide for solution turbulence when filling the ear canal. There may be any number of spray holes between 3 and 12, for example 4, 5, 6 or more spray holes that are distributed about the fill tip 310. The number of spray holes range from one to three or more and are evenly distributed one from the other (where there are three spray holes, they are spaced 120 degrees apart) to create turbulence in the ear canal 118. Further, the most distal portion of the fill system tip 310 is designed to face the tympanic membrane 122 such that during iontophoresis, the ear canal fills from the portions closest to the tympanic membrane out towards the outer ear 10 and air that has accumulated in the ear canal 118 will be evacuated though vent features 326 in the handle 316 as shown in FIG. 5. In an alternative embodiment, a valve (such as a one way valve or a check valve) may be integrated into the handle 316 such that fluid is instilled through the handle 316 and into the ear canal, and is the fluid is retained in the ear by the valve in the handle 316. No external fill system would therefore be required.

FIG. 13A is another embodiment of the device according to the invention. In this embodiment, the iontophoresis system of the invention comprises an earplug 1320, a fluid source 1340, a control unit 1342 and a ground pad 1346. Earplug 1320 is configured to be inserted into a patient's ear and remain there throughout the iontophoresis procedure. Earplug 1320 is mounted on a handle 1322 that is configured to be gripped during insertion of earplug 1320 into a patient's ear. Earplug 1320 also includes a flap 1328 that may be gripped and pulled to assist in removing earplug 1320 from the patient's ear. Of course, these features are mere examples, and any other suitable kinds of gripping features may be incorporated into earplug 1320. While only one earplug 1320 is shown, it should be understood that the iontophoresis system 1300 may have two earplugs 1320 that may be used simultaneously or sequentially.

Figure 13B:
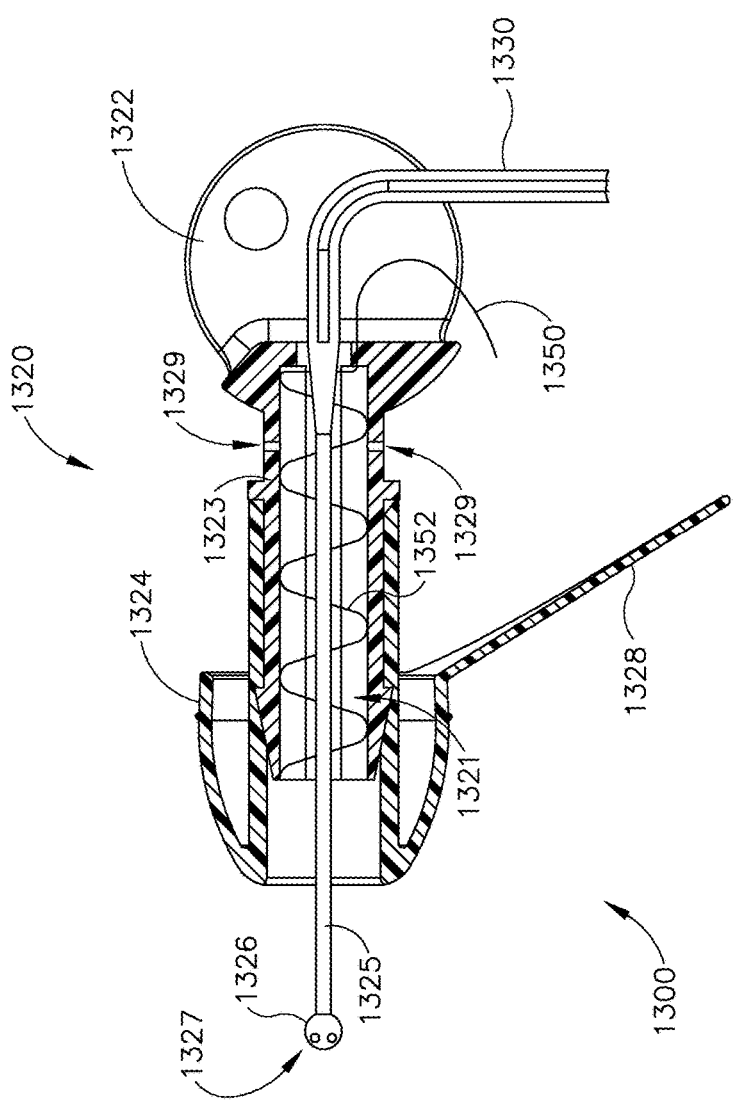
FIG. 13B is an enlarged cut-away view of the earplug and handle of the assembly shown in FIG. 13A.

As best seen in FIG. 13B, earplug 1320 includes a flexible sealing element 1324 and a distally projecting nozzle 1326. Sealing element 1324 is configured to provide a fluid tight seal against the patient's ear canal when earplug 1320 is inserted in the patient's ear canal. Nozzle 1326 is positioned to project into the patient's ear canal when earplug 1320 is inserted in the patient's ear canal, such that nozzle 1326 is spaced lateral to the tympanic membrane (TM). Nozzle 1326 has spray apertures 1327 and is secured to the distal end of a semi-rigid post 1325. Post 1325 provides a path for fluid communication from conduit 1320 to spray apertures 1327. Spray apertures 1327 are thus in fluid communication with fluid source 1340 via post 1325 and conduit 1330. Sealing element 1324 is secured to a rigid frame 1323 which defines gripping features on handle 1322. Sealing element 1324 and frame 1323 also together define a working channel 1321. Frame 1323 defines a plurality of vent paths 1329 in fluid communication with working channel 1321. Vent paths 1329 are configured to allow air to escape working channel 1321 while working channel 1321 fills with iontophoresis solution, yet are further configured to prevent iontophoresis solution from escaping working channel 1321 via vent path 1329 once working channel 1321 is filled with iontophoresis solution. An iontophoresis electrode 1352 in the form of a coil extends along at least part of the length of working channel 1321. It should be understood that iontophoresis electrode may have any other suitable configuration. Iontophoresis electrode 1352 is coupled with control unit 1342 via a cable 1350 and is thereby operable to be activated with a positive charge. Thus, control unit 1342 may activate iontophoresis electrode 1352 to provide a repulsive electromotive force to the iontophoresis solution delivered through aperture 1327 to drive the anesthetic of the iontophoresis solution into the tympanic membrane TM for anesthetization of the tympanic membrane.

Figure 15:
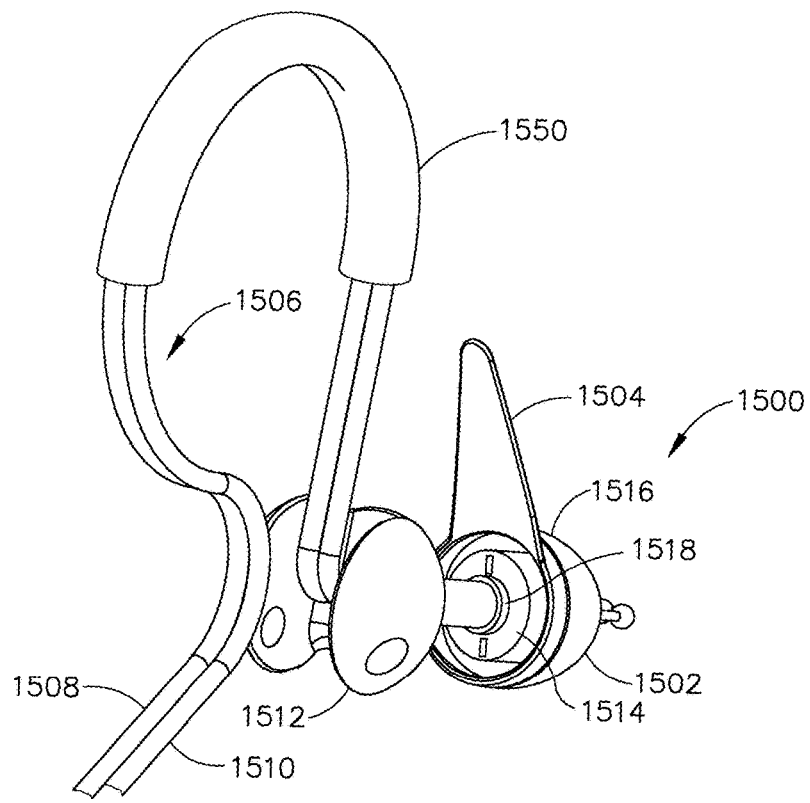
FIG. 15 is an enlarged view of the inside of the earplug of the earplug assembly shown in FIG. 13A and 13B.
Figures 16A, 16B, 16C, 16D:
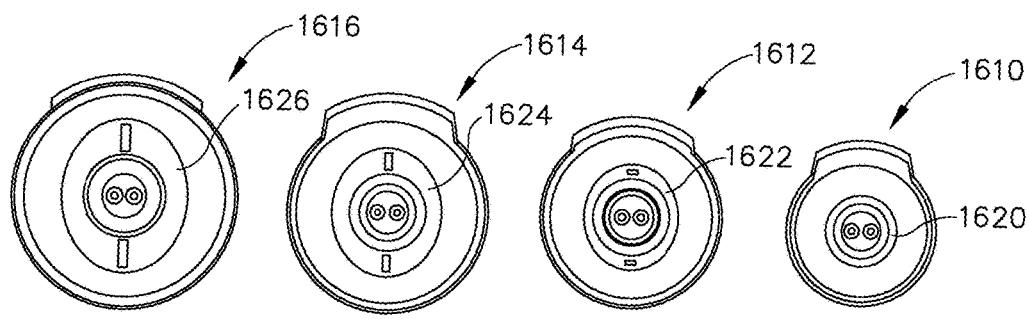
FIGS. 16A, 16B, 16C and 16D are top views of the inside of varying sized earplugs useful according to the invention.

Turning now to FIG. 15, in a particular embodiment, the earplug assembly 1500 is shown with a dome shaped earplug 1502, without a flange, but with a flap 1504 that can be gripped to remove the earplug from the ear canal as described above. In this particular embodiment, dual lumen tubing 1506 made of a soft polymeric material (in certain embodiments of Pea of 20 to 60 durometer) may be used to fill the ear canal with iontophoresis solution (the first lumen 1508) and to contain the iontophoresis wiring (the second lumen 1510). The handle 1512 is constructed such that the tubing is routed through the handle and exits the handle at an angle of between about 10 and 30 degrees and often about 15 degrees. The tubing is forced into the groove 111 behind the helix 108 of the ear 10 (see FIG. 1A). The tubing 1506 is then routed over the ear and terminates in a coiled section 1370 (see FIG. 13A). A sleeve 1550, made of higher durometer material that is smooth and slippery (in certain embodiments a polyolefin heat shrink thermoplastic material with a durometer above 50), may be included in a coaxial manner, surrounding a portion of the tubing 1506 above the ear, such that the earplug system 1320 may comfortably conform to different anatomies, that is, different ear sizes and head shapes and distribute the forces over a larger area above the ear, by allowing the tubing 1506 to slip within the sleeve 1506 and vary the amount of tubing 1506 that resides between the earplug 1502 and the polymeric sleeve 1550. A clip may be attached to the end of the coiled section 1370 and is clipped to the patient's clothing such that tension is applied to the earplug system 1320, protecting the system 1320 from interference by the patient or treatment provider and interruption of the iontophoresis procedure.

As noted earlier and shown in FIGS. 14A and 14B, pressure sensitive adhesive is applied to the dome shaped earplug 1502 in a variety of patterns. A pressure applicator 1514 is included on the inside portion 1516 of the dome shaped earplug 1502 and the handle 1512 is inserted into the base 1518 of the pressure applicator 1524. The pressure sensitive adhesive (PSA) is activated once it is in position in the ear canal by displacing or rotating handle 1512 and thereby putting pressure on the inside portion 1516 of the dome shaped earplug. As is shown in FIGS. 16A, 16B, 16C, and 16D, the base portion 1518 of the pressure applicator 1514 is shaped to match the ear canal anatomy. In the smallest sizes 1610 shown in FIG. 16D, the base portion 1620 is round, in the largest sizes 1616, the base portion 1626 is oval, the middle sizes 1612 (FIG. 16C) and 1614 (FIG. 16B) increase in ovalness from somewhat oval 1622 to mostly oval 1624 as the earplugs increase in size. The smallest earplugs may not require a pressure applicator as the gap between the handle stem and the umbrella portion of the plug is small enough that the handle stem can be deflected to active the glue by pivoting the handle.

Figure 17A:
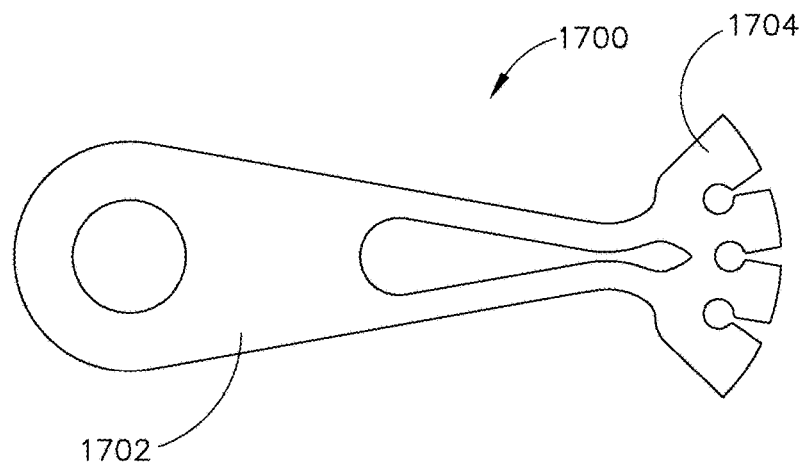
FIG. 17A is a top view of a liner useful with the earplugs of the invention.
Figure 17B:
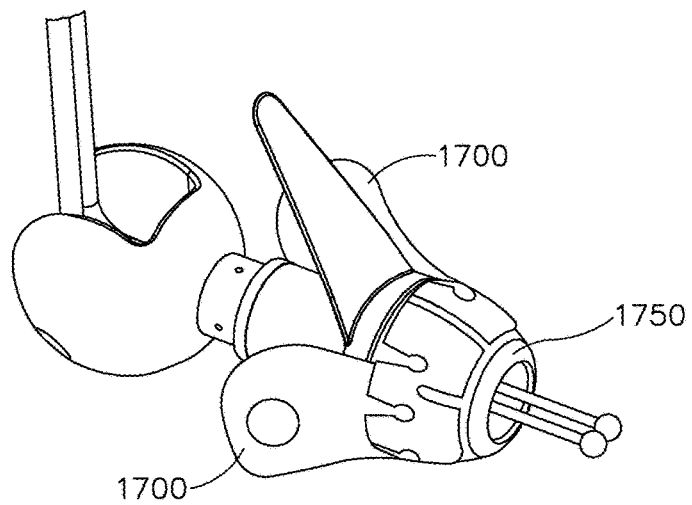
FIG. 17B is a perspective view of two liners in place over an earplug according to the invention.

As noted above with regard to earplug 300, a liner may be used to protect the PSA from adhering. The liner may be removed prior to final placement of the earplugs or it may be removed once final placement has been determined This latter type of liner is shown in FIGS. 17A and 17B. The liner 1700, shown in FIG. 17A is used to protect the PSA during storage and during insertion of the earplug 1750, shown in FIG. 17B. The liner has a gripping feature 1702 and an adhesive protector 1704. The liner may act as an insertion aid, giving the treatment provider the ability to reach a desired location before activating any of the PSA. In this way, the treatment provider can reposition and reinsert the earplug. As shown in FIG. 17B, the liner 1700 is designed to wrap around the profile of the dome of the earplug 1750 and fold back over onto itself In order to expose the PSA to the skin, the gripping feature 1702 is pulled back, rolling back the adhesive protector 1704, and allowing the PSA to touch the skin of the ear canal. In the embodiment shown in FIG. 17A, two liners 1700 are used to protect the PSA, but any number of liners from 1 to 4 may be used according to the invention.

Figure 8:
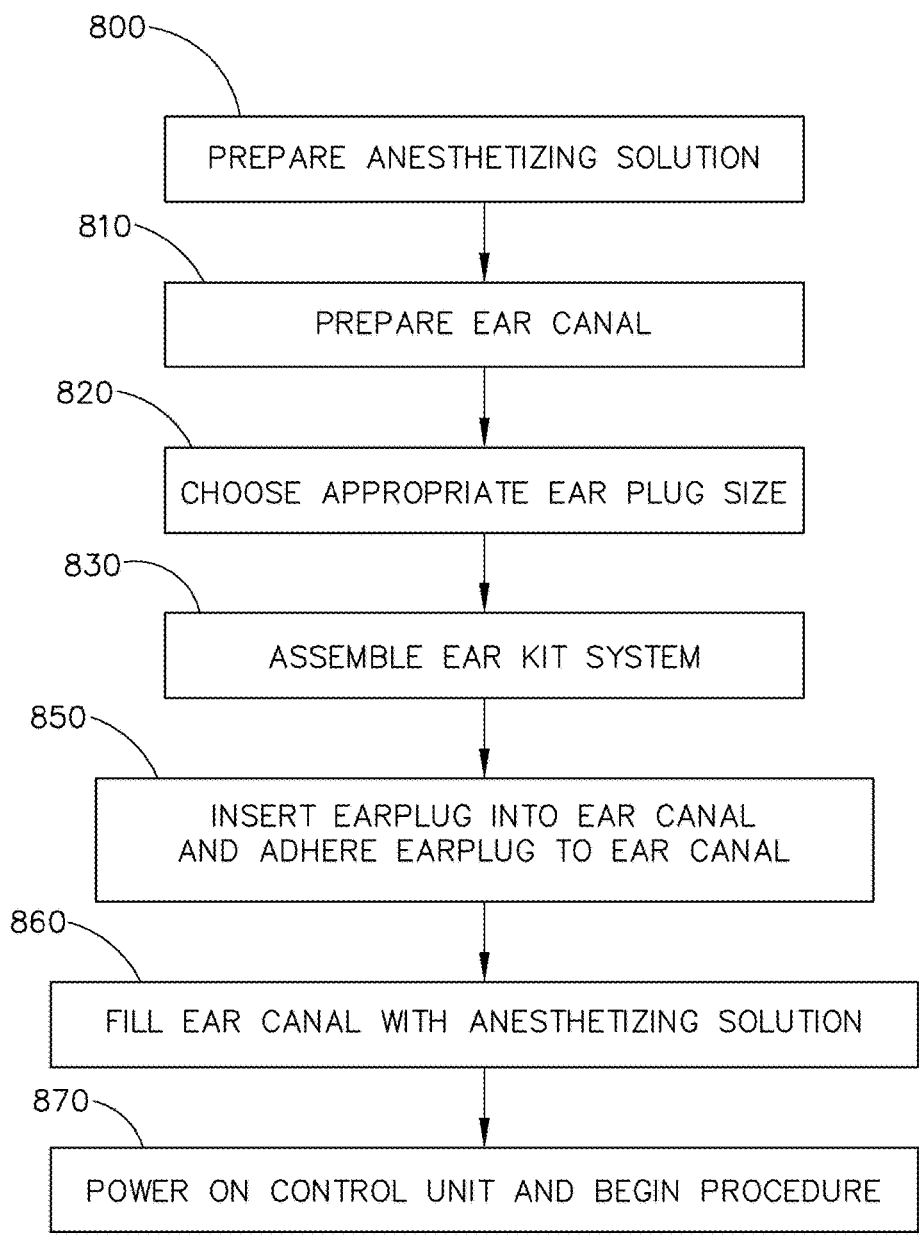
FIG. 8 shows a method according to the invention.

The method according to the invention is carried out according to FIG. 8. The anesthetizing solution is prepared (in this case a solution of 1:12,000 epinephrine, 3.3% lidocaine and 0.7% sodium bicarbonate but may be any appropriate combination thereof such as lidocaine, lidocaine plus epinephrine, or lidocaine plus epinephrine and sodium bicarbonate or other anesthetizing solution known in the art) and warmed to body temperature (800).

The ear canal is cleaned and prepared (810) using a standard ear cleaning technique, making sure that the tympanic membrane is not blocked by cerumen of observable size, The outside of the ear canal is wiped as well as the opening of the ear canal with rubbing alcohol to remove any oils or wax from the skin. The site is allowed to dry.

Figure 7:
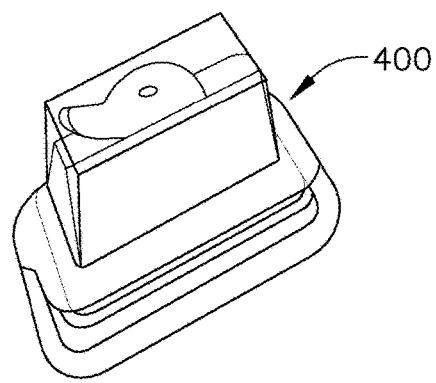
FIG. 7 shows a perspective view of a package for storing the earplug of FIG. 3.

The ear canal can be filled with anesthetizing solution in a number of different ways. The ear canal can be filled first by using a manual fill nozzle and then the earkit system 200 can be inserted to seal the ear canal and keep the fluid in place. Other methods for filling the ear canal will be described below. Following filling of the ear canal, the iontophoresis ear kit system 200 is then prepared for placement on the patient as follows. As previously described above with regard to FIG. 2, an earplug sizer 234 is placed into a patient's ear canal to determine the appropriate earplug size for the size and shape of the patient's ear canal (820). The appropriate ear plugs 300 are removed from the package 400 (see FIG. 7) and the PSA 320 is exposed. The package 400 is made so as to prevent any dust exposure of the adhesive and is designed in such a way to enable the removal of the earplugs 300 with the grips 330 from the package 400 and placement onto the handles 214a and 214b. In the embodiment shown in FIG. 7, the package 400 is designed so that the earplug 300 is positioned with the dome portion 302 facing up such that the adhesive is not in contact with any portion of the package. In an alternative design, the dome portion may be seated in a cup-shaped packaging system, such that the adhesive is in contact with the package. The earplugs 300 are then positioned onto the handles 214a or 214b of the fill tube and wire system 212 (830). In an alternative embodiment, using the earplug system 1320 shown in FIG. 13A, the device is placed in the ear canal, the ear canal is filled with the iontophoresis solution that is supplied through the dual lumen tubing 1304 and the iontophoresis procedure is continued as further described below.

The earplugs 300 are carefully placed into the patient's ears such that the ear canal is sealed against leakage of fluid from the ear canal (850). The fill tube and wire system 212 are routed behind the ear and anchored behind the patient's head such that they remain out of the patient's and treatment provider's way. The return electrode patch 226 is connected to the iontophoresis ear kit system 200 via the return electrode snap 227 on the electrode patch 206 and the return electrode connector (not shown) on the cable 210. The syringe is depressed in order to fill the ear canal with anesthetizing solution (860). The return electrode patch 226 is placed on the patient's skin and the control unit 228 shown in FIG. 2 may be connected to the control unit connector 229 on the fill tube and wire system 212 shown in FIG. 2 and the control unit 228 may be clipped to the patient's or the parent's clothing.

The battery tab located on the back of the control unit 228 case is removed. Empty status bars should appear on screen once the device is powered on. To start the iontophoresis procedure, the control unit is activated by pressing the yellow button and/or the blue button on the control unit 228 and holding for 2 seconds (870). Each button controls an independent channel, with button colors corresponding to the colors of the left and right sides of the headset. A short beep confirms when a button has been activated. The control unit 228 is clipped to the patient's or the parent's clothing. The status bars will fill up to indicate each channel's progress toward completion. A typical procedure takes approximately 10 minutes, with each status bar segment representing approximately 20% of procedure time. A flashing segment indicates that current is running; a solid segment indicates the portion already completed. To pause the procedure, the button for the appropriate channel is pressed and held for 2 seconds. The pause symbol and status bar segment will both flash and then turn solid when current delivery has stopped. To resume the procedure, the same button is pressed and held for 2 seconds. The control unit 228 will play a long beep when each channel (yellow or blue side) has completed delivering a full dose. The status bars will also turn completely solid to indicate that full charge has been delivered through each channel. Once the tympanic membrane is anesthetized, to deactivate the control unit, the button for the appropriate channel is pressed and held for 2 seconds.

Figure 9D:
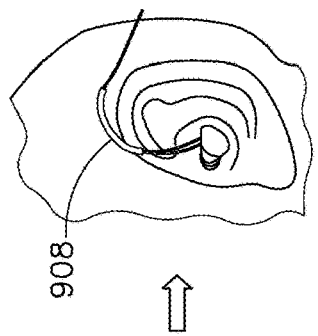
FIGS. 9A, 9B, 9C and 9D show perspective views of a method for filling the ear canal according to the invention.
Figure 9C:
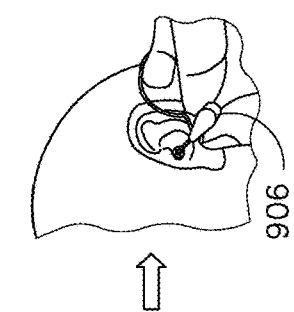
Figure 9B:
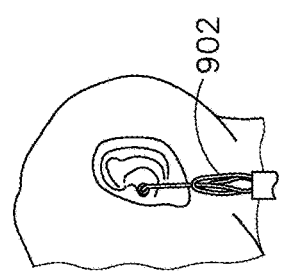
Figure 9A:
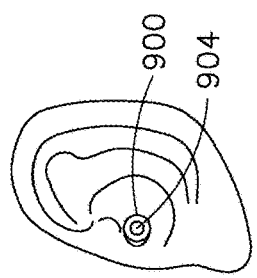

Other methods of filling the ear canal will further be described with regard to FIGS. 9A, 9B, 9C and 9D and FIGS. 10A, 10B, 10C, 10D and 10E. As shown in FIGS. 9A, 9B, 9C and 9D, the earplug 900 can be inserted by using an earplug insertion tool (not shown in the figure) and then secured and sealed to the ear canal (see FIG. 9A). The ear canal can then be filled with the drug solution using a manual fill system 902 or any other means of filling the ear canal, by inserting the fluid through the central lumen 904 of the earplug 900 (FIG. 9B). The central lumen 902 of the earplug 900 can then be sealed by inserting the elbow-handle 906 through the lumen (FIG. 9C). The tube and the wire 908 can then be routed behind the ear (FIG. 9D)

In another method for filling ear canal according to the invention, an earplug 1000 can be loaded on to a speculum 1002 as shown in FIG. 10A. The speculum 1002 can then be used for positioning and insertion of the earplug 1000 in the ear canal (see FIG. 10B). After the earplug is seated in place the ear canal can be filled with fluid by using the speculum as an aid and guide and filling with a manual fill system 1004 (FIG. 10C). After the ear canal has been completely filled with the fluid solution, the speculum 1002 can be removed, keeping the earplug 1000 in place (FIG. 10D). The ear kit handle 1006 can then be inserted in the earplug 1000 to seal the earplug and provide contact between the drug solution and the electrode present in the ear kit handle 1006 and the tube and wire 1008 can be routed behind the ear (FIG. 10E).

In a further aspect, the fill tube and wire system 212 may be useful for delivering a drug solution to the ear canal for treating the ear canal It may be used for anesthetizing the ear canal or tympanic membrane or for delivering solutions for other therapeutic purposes. Such solutions include but are not limited to antifungal or antibacterial agents such as benzalkonium chloride, boric acid, acetic acid, and clotrimazole, anti-inflammatory agents such as beclamethazone and antibiotic and steroids such as betnesol, prednisilone sodium phosphate, gentamycin, neomycin, and quinolenes, astringent agents such as aluminum acetate, ceruminolytics such as sodium chloride solution, hydrogen peroxide or sodium bicarbonate solution.

The invention has been described with reference to certain examples or embodiments of the invention, but various additions, deletions, alterations and modifications may be made to those examples and embodiments without departing from the intended spirit and scope of the invention. For example, any element or attribute of one embodiment or example may be incorporated into or used with another embodiment or example, unless otherwise specified or if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

The invention claimed is:

1. An earplug comprising:
   a dome-shaped portion for insertion into an ear canal, said dome-shaped portion having an outside surface and an inside surface;
   a pressure sensitive adhesive positioned on the outside surface of the dome-shaped portion and configured to contact a surface of the ear canal to define a space in the ear canal between the dome-shaped portion and a tympanic membrane such that a solution delivered into the space can be retained in the space for a period of time; and
   a liner in a folded configuration configured to protect the pressure sensitive adhesive when the dome-shaped portion with the pressure sensitive adhesive positioned thereon is inserted into the ear canal, the liner configured to unfold after the dome-shaped portion is positioned in the ear canal such that the pressure sensitive adhesive is exposed for contact with the surface of the ear canal.

2. The earplug of claim 1, further comprising a flange surrounding the dome-shaped portion.

3. The earplug of claim 2, wherein the flange surrounds 180 to 360 degrees of the dome-shaped portion.

4. The earplug of claim 2, wherein the flange includes notches.

5. The earplug of claim 1, wherein the solution includes at least one of: an anesthetizing solution, an antibacterial solution, an antifungal solution, an anti-inflammatory solution, or a ceruminolytic solution.

6. The earplug of claim 5, wherein the solution is an anesthetizing solution including at least one of: lidocaine; a combination of lidocaine and epinephrine; or a combination of lidocaine, epinephrine, and sodium bicarbonate.

7. The earplug of claim 1, further comprising a shaft portion for connection to a fill system through which the solution is delivered into the space in the ear canal, the dome-shaped portion surrounding a portion of the shaft portion.

8. The earplug of claim 1, wherein the pressure sensitive adhesive includes at least one of: a silicone, an acrylic, butyl rubber, ethylene-vinyl acetate, natural rubber, a nitrile, or a styrene block copolymer.

9. The earplug of claim 1, wherein the liner has (1) a first portion that is configured to wrap around a portion of the dome-shaped portion to cover the pressure sensitive adhesive and (2) a second portion that is configured to fold over and onto the first portion.

10. The earplug of claim 1, wherein the liner includes a gripping element configured to be pulled to unfold the liner and remove the liner from the earplug.

11. A system, comprising:
   an earplug for use in retaining a solution in an ear canal of the human patient, the earplug comprising:
      a dome-shaped portion for insertion into the ear canal, the dome-shaped portion having an outside surface and an inside surface; and
      a pressure sensitive adhesive positioned on the outside surface of the dome-shaped portion and configured to contact a surface of the ear canal to define a space in the ear canal between the dome-shaped portion and a tympanic membrane such that the solution can be retained in the space for a period of time;
   a fill system configured to deliver the solution into the space in the ear canal; and
   a liner including a gripping element, the liner configured to protect the pressure sensitive adhesive when the dome-shaped portion with the pressure sensitive adhesive positioned thereon is inserted into the ear canal to enable the dome-shaped portion to be positioned in the ear canal before the liner is removed by pulling on the gripping element.

12. The system of claim 11, further comprising vent features.

13. The system of claim 12, wherein the vent features include at least one of: a vent hole or a vent slit.

14. The system of claim 11, further comprising a flange surrounding the dome-shaped portion.

15. The system of claim 11, wherein the fill system further includes a fill tip including a plurality of spray holes.

16. The system of claim 11, wherein the solution includes a therapeutic agent, the system further comprising an electrode to supply a current to drive the therapeutic agent, via iontophoretic delivery, into the tympanic membrane.

17. A method, comprising:
positioning a dome-shaped portion of an earplug in an ear canal of a human patient, the dome-shaped portion configured to fit against a surface of the ear canal and including a pressure sensitive adhesive positioned thereon, the pressure sensitive adhesive covered by a liner;
removing, after the dome-shaped portion is positioned in the ear canal, the liner by rolling back a portion of the liner to expose the pressure sensitive adhesive such that the dome-shaped portion adheres to the surface of the ear canal;
delivering, via a fill system, a solution including a therapeutic agent into a space between the earplug and a tympanic membrane; and
supplying an electric current to the solution to deliver the therapeutic agent to the tympanic membrane.

18. The method of claim 17, wherein the therapeutic agent includes at least one of: lidocaine; a combination of lidocaine and epinephrine; and a combination of lidocaine, epinephrine, and sodium bicarbonate.

19. The method of claim 17, further comprising, prior to delivering the solution into the space, warming the solution to body temperature.

20. The method of claim 17, wherein the liner includes a gripping element, and the removing the liner includes pulling on the gripping element such that the portion of the liner covering the pressure sensitive adhesive is rolled back to expose the pressure sensitive adhesive.

* * * * *